Figure 6:
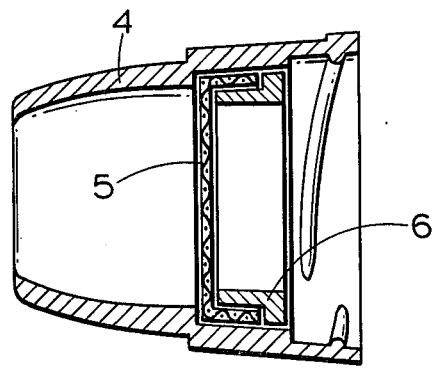

United States Patent [19]

James

[11] 4,117,844
[45] Oct. 3, 1978

[54] DEVICE FOR DISPENSING MEDICAMENTS
[75] Inventor: Michael James, Welwyn Garden City, England
[73] Assignee: Allen & Hanburys Limited, London, England
[21] Appl. No.: 767,512
[22] Filed: Feb. 10, 1977
[30] Foreign Application Priority Data
Feb. 11, 1976 [GB] United Kingdom ............... 5353/76
[51] Int. Cl.$^2$ ............................................. A61M 15/00
[52] U.S. Cl. .................................. 128/266; 128/208; 222/83.5; 222/193
[58] Field of Search ...................... 128/208, 206, 266; 222/83.5, 86, 88, 193

[56] References Cited
U.S. PATENT DOCUMENTS

| | | | |
|---|---|---|---|
| 3,918,451 | 11/1975 | Steil | 128/208 |
| 4,013,075 | 3/1977 | Cocozza | 128/208 |

Primary Examiner—Henry J. Recla
Attorney, Agent, or Firm—William R. Liberman

[57] ABSTRACT

An inhalation device by which powdered medicaments can be self-administered to a patient comprising a chamber arranged to receive a capsule containing the powdered medicament. At least one air inlet aperture leading into the chamber. A nozzle through which air can be inhaled leads from the chamber. A magazine is slidable and rotatable in the chamber and has a longitudinal capsule loading receptacle arranged so that a capsule inserted therein will have an end portion projecting from the receptacle into the chamber. A knife is fixed in the chamber in such a position that rotation of the magazine with respect to the chamber will cause the projecting portion of a capsule located in the receptacle to engage a cutting edge of the knife thereby to sever the projecting portion of the capsule from the remainder of the capsule. A capsule ejecting member is arranged inside the chamber in a position such that it will enter the capsule loading receptacle when such receptacle has first been registered with the member by appropriate rotation of the magazine with respect to the chamber and then by sliding the magazine with respect to the chamber thereby to eject the remaining part of the capsule from the loading receptacle into the chamber so that the contents of the capsule may be inhaled through the nozzle.

8 Claims, 8 Drawing Figures

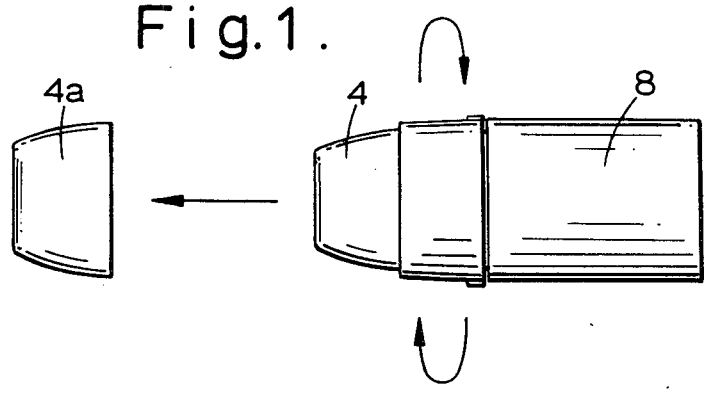
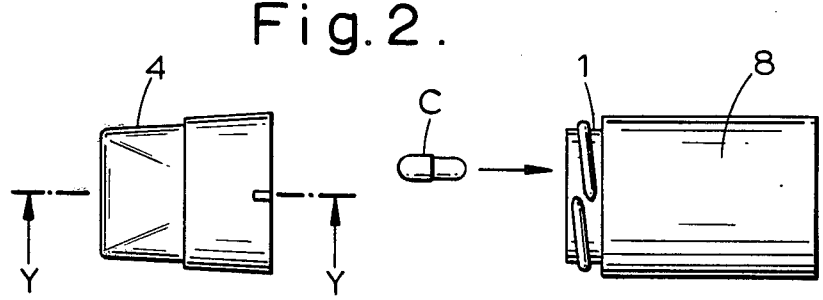
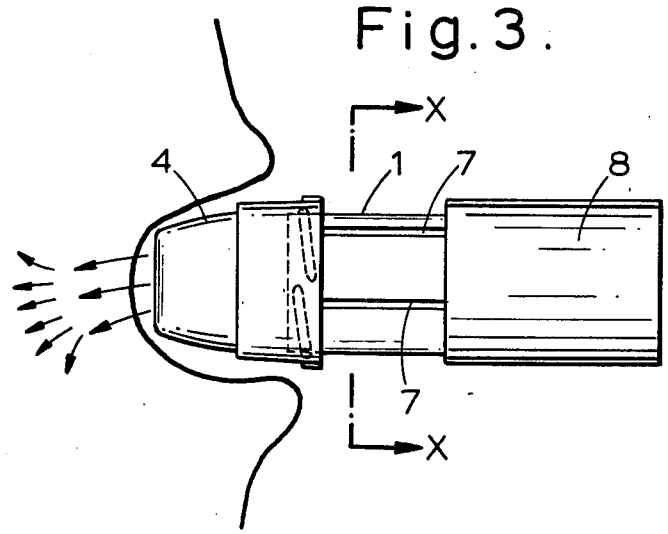

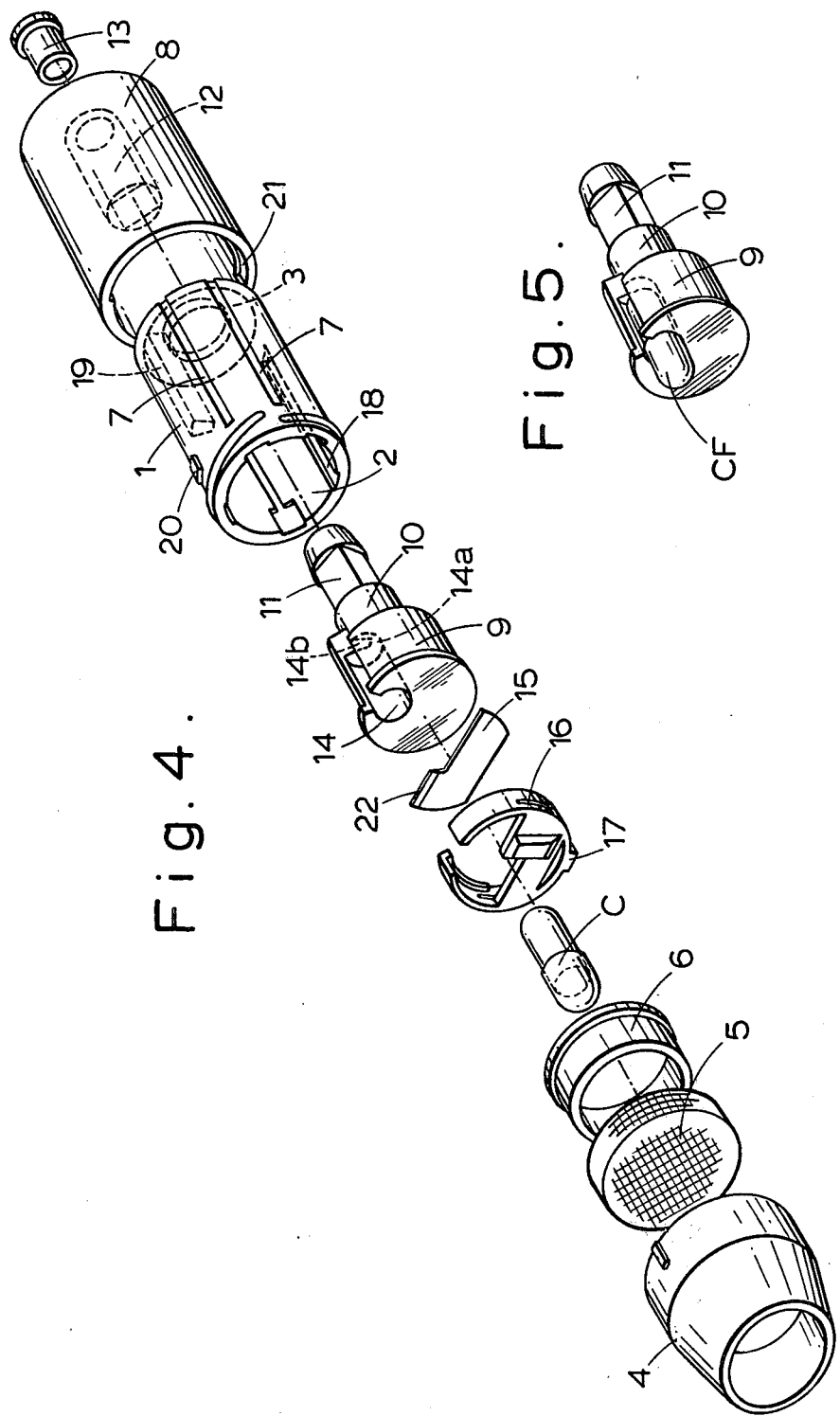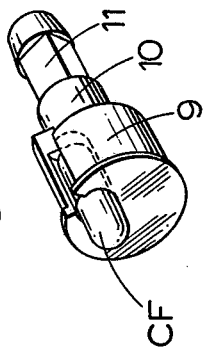

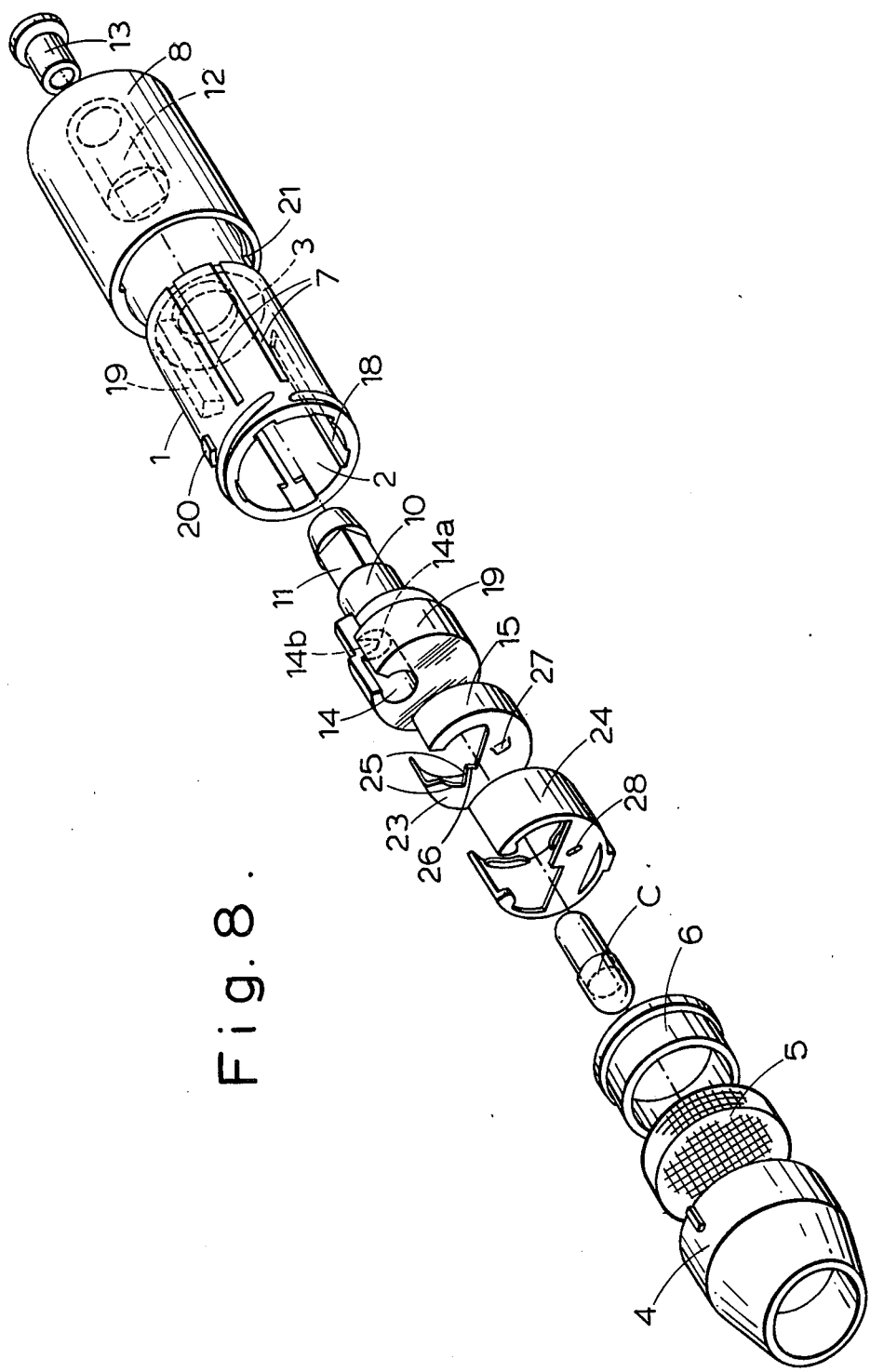

DEVICE FOR DISPENSING MEDICAMENTS

BACKGROUND OF THE INVENTION

It is well known to administer powdered medicament to the lung bronchioles of a patient by means of inhalation devices having mouthpieces which enable the medicament to be inhaled through the mouth of the patient. The medicament is supplied in capsules which are inserted in the device and pierced prior to use after which inhalation through the mouthpiece will cause the powdered medicament to be released from the capsule and passed to the patient. An object of the present invention is to provide an improved such inhalation device which is particularly, but not exclusively, suitable for use in the treatment of asthmatic patients.

BRIEF DESCRIPTION OF THE ACCOMPANYING DRAWINGS

Figure 7:
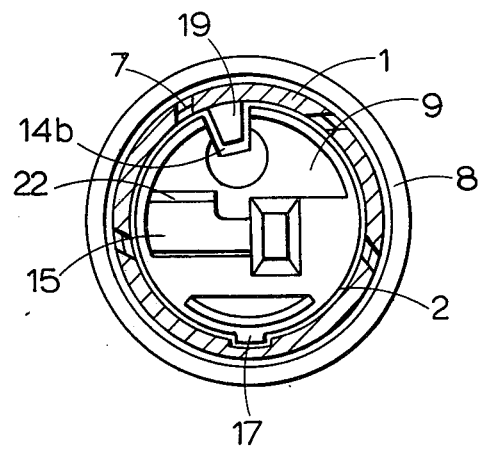

FIG. 1 is an elevation of an inhalation device according to this invention,

FIG. 2 is an elevation of the device illustrated in FIG. 1 with a mouthpiece removed, FIG. 3 is a diagrammatic representation of the device in use, FIG. 4 is an exploded perspective view of the device, FIG. 5 is a scrap view illustrating a capsule in a magazine of the device, FIG. 6 is a sectional view on the line Y—Y of FIG. 2, FIG. 7 is a sectional view on the line X—X of FIG. 3, and FIG. 8 is an exploded perspective view of a modification.

In the drawings, like parts are designated by like reference numerals.

DESCRIPTION OF ONE EMBODIMENT

In the embodiment of the invention illustrated in FIGS. 1 - 6, an inhalation device comprises a cylindrical body 1 the interior of which defines a capsule receiving chamber 2. The body 1 has an end wall 3 at one end and is open at the other end. For convenience of description, the end of the body having the end wall 3 is herein considered to be the rear end and the open end is considered to be the front end. A nozzle in the form of a removable mouthpiece 4 is screwed on the front end of the body. A dust cap 4a is removably fitted on the mouthpiece 4. A patient can inhale through this mouthpiece to withdraw powdered medicament from a capsule C which has been divided into a plurality of parts and placed in the chamber 2 as hereinafter to be described. The rear end of the mouthpiece 4 has a grid or guard 5 which prevents the parts of a divided capsule, but not the powdered medicament, being aspirated through the mouthpiece when the patient inhales. The grid or guard 5 is cup-shaped and is secured in the mouthpiece 4 by a retaining ring 6. The parts of a divided capsule tend to rotate on the grid or guard as air is drawn through the chamber 2 and mouthpiece 4 so that if, as is preferred, the grid or guard 5 has a rough surface such rotation assists in vibrating the parts of the capsule and in dispersing the powder.

The wall of the body 1 has a plurality of air inlet slots 7 disposed lengthwise of the body. If desired, these slots 7 are arranged in an area extending only around a major part (say about two thirds of the length) of the periphery of the body. Conveniently, there are not less than two nor more than four slots. These slots 7 communicate with the chamber 2 and are angled with respect to a diametrical chord of the chamber. Thus, when air is inhaled through the mouthpiece 4, it will cause air to pass through the chamber 2 in such a way as violently to agitate parts of a capsule C contained in the chamber. This agitation will cause the powdered medicament still in the capsule parts to be released and allow it to be dispersed in the turbulent airflow.

The resulting powder dispersion will be aspirated through the mouthpiece 4 into the patient.

An operating sleeve 8 which defines a handle is telescopically slidable over the rear end portion of the body 1 and is also rotatable thereon. A magazine 9 (best illustrated in FIG. 4) is arranged inside the body and has an axial shaft 10 with flat surfaces 11 which mate with complementary surfaces in a passage 12 in the sleeve 8 so that the sleeve and magazine are slidable and rotatable together as a unit. The passage 12 is conveniently closed by an end plug 13. The magazine 9 has a capsule loading passage or receptacle 14 extending lengthwise of the magazine and body, but offset from the axis of the body and magazine. This loading receptacle 14 is open at the front but is closed at the rear by an end wall 14a having a slot 14b. A capsule C containing a powdered medicament to be inhaled can be inserted into the open end of the capsule loading receptacle 14 after the mouthpiece 4 has been removed from the body 1. The length of the receptacle 14 is such that when the capsule has been inserted in the receptacle 14, a front end portion CF (FIG. 5) of the capsule will project from the front of the receptacle 14. When the capsule has been inserted in the loading receptacle 14 the mouthpiece 4 is replaced.

A knife 15 is mounted inside the body 1 in a mounting or retaining ring 16. This mounting ring 16 is a sliding fit inside the body 1 and has a key 17 engaged in a keyway 18 forming part of the inside of the body 1. The ring 16, can therefore, slide with respect to the inside of the body 1, but it cannot rotate. The ring 16 is connected with the front end of the magazine in such a way that the magazine can rotate with respect to the ring 16, but the ring and magazine are slidable together.

A capsule ejector fin 19 is fixed in the body 1 behind the magazine 9 in such an angular position that when the sleeve 9, and therefore the magazine 9, is moved to the open or operative position and the capsule loading receptacle 14 is registered with the fin 19, the fin will enter the loading receptacle 14 thereby to eject the capsule through the open front end of the receptacle 14 into the chamber. The body 1 has a flat projection or peg 20 which fits into an internal groove 21 in the sleeve 8. The ends of the groove 21 form abutments which are engageable by the projection 20 thereby to limit rotation of the sleeve 8 with respect to the body 1.

In operation, a capsule C containing medicament to be inhaled is loaded into the capsule loading receptacle 14 of the magazine 9 and the mouthpiece 4 is then screwed on the body 1. The handle defining sleeve 8 is then rotated approximately one half turn. Such rotary movement of the sleeve will also rotate the magazine 9 and the capsule C contained in the loading receptacle 14 of the magazine whereupon the knife 15 and loading receptacle 14 are so positioned with respect to one another that such rotation will engage the projecting portion of the capsule with a cutting edge of the knife 15 thereby to sever the projecting portion of the capsule from the remainder of the capsule. As shown in FIGS.

1 – 7, the knife 15 is in the form of a stepped blade with a cutting edge 22 which cuts the capsule. After the capsule has been cut, the sleeve 8 and magazine 9 are then rotated in the opposite direction back to the original position. This will cause the capsule loading receptacle 14, which is open at both ends, to be registered with the capsule ejector fin 19. When the sleeve 8 is correctly positioned, it is slid to its open or operative position and during such movement the fin 19 will enter the capsule loading receptacle 14 of the magazine 9 and in so doing will press against the rear end of the capsule and push it out of the front end of the loading receptacle 14 into the chamber 2. This movement also uncovers the air inlet slots 7 and the patient can then inhale through the mouthpiece 4 so as to inhale the powdered medicament. When the inhalation has been completed, the patient can unscrew the mouthpiece 4 to remove the parts of the spent capsule and another capsule can be inserted in the capsule loading receptacle 14 ready for another inhalation.

FIG. 8 illustrates a device with a modified knife 15. In this modification, the knife 15 is in the form of a cup 23 which is retained in position in the body 1 by retaining ring or cup 24. The blade cup 23 has a cut-away portion in its base to provide cutting edges 25 with projecting fang 26. The base of the cup-shaped blade has a tab or projection 27 engaged in a slot 28 in the base of the retaining ring or cup 24 to hold the blade against rotation. This arrangement provides a more positive anchoring of the capsule C during a cutting operation than does the arrangement of FIG. 1 – 7 and also makes it possible for the cutting edges of the blade to be less sharp.

The sleeve 8 in both the embodiments of the invention described constitutes a handle by which the device may be held. If desired, the axial shaft 10 may be extended to project from the rear end of the body 1 and terminate in a handle in the form of a knob. The device is then not provided with a sleeve 8.

The inhalation device of this invention is primarily intended for the oral administration of a medicament, in which case the nozzle is, as hereinbefore described, in the form of a mouthpiece which may be inserted in the mouth of a patient. However, the device may be used for the nasal administration of a medicament in which case the nozzle is constructed so that it may be inserted in a nostril of a patient.

What is claimed is:

1. An inhalation device for administering to a patient medicaments contained in a capsule, said device comprising a chamber arranged to receive a capsule containing a powdered medicament, at least one air inlet aperture leading into said chamber, a nozzle communicating with said chamber through which air can be inhaled therefrom, a magazine attached to said chamber and slidable and rotatable along and about a longitudinal axis in said chamber and having a longitudinal capsule loading receptacle transversely offset from said axis, said receptacle including means such that a capsule inserted therein will have an end portion projecting from said receptacle into said chamber, a knive coupled to and located in said chamber adjacent said receptacle and having a cutting edge movable across a path intercepting the longitudinal axis of said receptacle whereby rotation of said magazine with respect of said chamber will cause said projecting portion of said capsule located in said receptacle to engage said cutting edge of said knife thereby to sever said projecting portion of said capsule from the remainder of said capsule, and capsule ejecting means mounted on and arranged inside said chamber in a position transversely offset from said longitudinal axis in said chamber and means for rotating and sliding magazine whereby it will enter said capsule loading receptacle when such receptacle has first been registered with said ejecting means by appropriate rotation of the magazine with respect to said chamber and then by sliding said magazine with respect to said chamber thereby to eject the remaining part of said capsule from said loading receptacle into said chamber so that the contents of said capsule may be inhaled through said nozzle, and means for preventing the parts of the severed capsule leaving the chamber when the patient inhales through the nozzle.

2. A device as claimed in claim 1, comprising a cylindrical body the inside of which defines said chamber, said means for rotating and sliding includes telescopically engaging said body, said magazine being cylindrical and having a shaft which extends out of a rear end of said body and is connected with said sleeve so as to be rotatable and slidable with said sleeve.

3. A device as claimed in claim 2 in which said sleeve has proximate its front edge an internal peripheral groove terminating in end shoulders and said body has a projection slidably longitudinally releasably engaging said groove whereby relative rotation between said sleeve and said body is limited.

4. A device as claimed in claim 3 including a mounting ring rotatably mounted on said magazine and slidably engaging and fixed against rotation relative to said body, said knife being secured to said mounting ring.

5. A device as claimed in claim 4, wherein said knife has a cup-shaped blade secured to said mounting ring, the base of the said cup-shaped blade having a cut-away portion providing a curved cutting edge, with a fang.

6. A device as claimed in claim 4, wherein said receptacle has an end wall which limits movement of a capsule into the receptacle, said end wall having a recess through which said ejector member can pass.

7. A device as claimed in claim 4, wherein said nozzle is a mouthpiece removably fitted on one end of said body, a cup-shaped perforated guard being arranged inside said mouthpiece and secured therein to prevent parts of a capsule in said chamber being withdrawn when air is inhaled through said mouthpiece.

8. A device as claimed in claim 1 having a handle by which said device may be held.

* * * * *